United States Patent [19]
Ball

[11] Patent Number: 5,841,034
[45] Date of Patent: Nov. 24, 1998

[54] BONDED JOINT ANALYSIS

[75] Inventor: Andrew S Ball, Farnborough, Great Britain

[73] Assignee: British Aerospace Public Limited Company, Hampshire, Great Britain

[21] Appl. No.: 880,725

[22] Filed: Jun. 23, 1997

Related U.S. Application Data

[63] Continuation of Ser. No. 675,835, Jul. 5, 1996, abandoned.

[51] Int. Cl.⁶ ........................................................ G01L 1/24
[52] U.S. Cl. ................................. 73/800; 73/827
[58] Field of Search .............................. 73/800, 826, 827, 73/828, 830

[56] References Cited

U.S. PATENT DOCUMENTS

| | | | |
|---|---|---|---|
| 4,461,536 | 7/1984 | Shaw et al. | 73/800 |
| 4,789,236 | 12/1988 | Hodor et al. | 73/800 |
| 5,250,802 | 10/1993 | Runner | 73/800 |
| 5,265,475 | 11/1993 | Messinger et al. | 73/800 |

OTHER PUBLICATIONS

"The UltraSPARC Processor—Technology White Paper; The UltraSPARC Architecture," Nov. 14, 1995, Sun Microsystems, Inc., Palo Alto, CA.

*Primary Examiner*—Max H. Noori
*Attorney, Agent, or Firm*—Cushman Darby Cushman IP Group of Pillsbury Madison & Sutro LLP

[57] ABSTRACT

The present invention relates to a method of testing and/or monitoring structural adhesively bonded joints by the introduction of transducers into the stress or strain field effected by the movement of said adhesively bonded joints under load, such that the load transfer characteristics between the bonded materials and the adhesive can be recorded thus allowing the quantification of the integrity of the adhesive bond lines in such joints. The method assesses the integrity of the bond by comparing the difference in maximum and minimum ratios and curve perameters relating to stress and strain with those of the "at assembly" values.

1 Claim, 1 Drawing Sheet

BONDED JOINT ANALYSIS

This is a continuation of application Ser. No. 08/675,835, filed on Jul. 5,1996, which was abandoned upon the filing hereof.

BACKGROUND OF THE INVENTION

This invention relates to the field of testing and monitoring structural characteristics of bonded joints and more specifically to a method of assessing and quantifying the integrity of adhesive bond lines in such joints.

The testing and/or monitoring of the structural integrity of load carrying joints is one of the most important areas of engineering research. The ability to understand how structural joints are performing in service gives engineers the ability to refine and tailor their designs to maximize the strength of such structures, while at the same time minimizing their weight.

The advent of structural adhesives and the use of composite materials have, in industries such as aerospace, revolutionized structural material utilization, with the number of available materials and adhesives for use in structural applications increasing markedly. The use of such technology has brought with it problems related to the inspectability of bonded joints due to there being no outwardly visible sign of connection (i.e. bolt or rivet heads protruding), so alternative and more costly methods have had to be utilized to ensure the integrity of such assemblies.

Various methods of structural health monitoring have been proposed, but the principle by which such methods give indications of reducing mechanical joint properties lies in their identification of areas of increased local strain or displacement. Such techniques are able to give indications of possible degradation of joint integrity, but can only give indications of possible areas of increased strain or displacement due to the nature of the state of the art transducers.

State of the art methods utilized in the inspection of bonded structural joints involve the use of non-destructive test (NDT) techniques which, by the very nature of the scanning equipment required, can take a considerable amount of time and effort to undertake effectively. Additional problems occur when bonded joints are required to be inspected which are not readily accessible for the introduction of an NDT scanning head and therefore costly disassembly of areas of surrounding structure may be required.

SUMMARY OF THE INVENTION

Our invention offers a method of analyzing the integrity of bonded structural joints by utilizing sensor means capable of detecting the characteristics of load path/transfer through a bonded joint, without the requirement for such joints to be accessible for visible inspection. Additionally our method of analyzing the integrity of the bond line utilizes the comparison of measured joint properties, with that of the original, "as assembled" joint properties.

Accordingly there is provided a method of analyzing the integrity of adhesively bonded structural joints under load, including the steps of;

locating a transducer means in proximity of the joint, the transducer means being so disposed in relation to the bonded joint that parameters indicative of load transfer characteristics between a bonded material and an adhesive can be recorded in response to the application of load, the transducer means comprising a fiber optic cable with an integrated optical grating means extended in parallel with the applied load for indicating strain characteristics along a bond line of the bonded joint, the load characteristics being measured by optical time domain reflectometry recording reference parameters indicative of the load transfer characteristics between the bonded material and the adhesive of said joint under the application of a reference load after assembly of said bonded joint, subsequently recording service parameters indicative of the load transfer characteristics between the bonded material and the adhesive of said joint under the application of a service load, and comparing said reference parameters with said subsequently obtained service parameters to determine the integrity of the bond.

BRIEF DESCRIPTION OF THE DRAWINGS

The invention will now be described by way of example only in which reference will be made to the following drawings:

In FIG. 1, a structural bonded lap joint 1 is shown in an assembled condition, having two members 2,4 bonded by a layer of adhesive 6. The thickness of the structural adhesive 6 is shown as (t), and would typically be in the order of 0.1–0.2 mm. A co-ordinate axis system 8 is shown for reference in FIG. 2 along with typical applied loads (p) 10

FIG. 2 shows the typical strain and load ($\epsilon$, p) distribution (y) with distance (x) for the bonded lap joint I for an applied load 10 in direction (p), with reference to the given co-ordinate axis system 8. At x=0, the graph shows the strain or load at zero 12. As more of the load is attracted into the relatively less stiff adhesive 6 the strain or load increases rapidly to a peak 14 and then gradually decreases to a minimum as x increases along the length of the bondline at the x centreline 16. Due to the mechanical symmetry of the example joint, the strain or load then increases with increasing x position to another peak 18, before falling again to zero, 20, at the corresponding edge of the bond line, 6.

FIG. 3 shows a bonded structural lap joint 1, with an optical fibre 26 embedded within the adhesive bondline 6. The fibre 26 is attached to, and/or comprises a transducer means 28, which is so disposed so as to be capable of responding in a measurable way, and to produce some form of recordable output, to indicate the load transfer and distribution profile across the width of the bondline 6, due to the application of a load (p) 10. A typical example of such profile is shown in FIG. 2. The transducer/fibre 28/26, is connected to a processing/ recording/display means 30, which is capable of processing the output of the fibre/transducer means 28 in response to the applied load (p) 10. This method of analysis therefore facilitates the recording of the load and/or strain distribution across the fibre 6, so as to enable a record of the particular load transfer characteristics of the bondline adhesive under evaluation to be made.

DETAILED DESCRIPTION OF THE INVENTION

Figure 1:
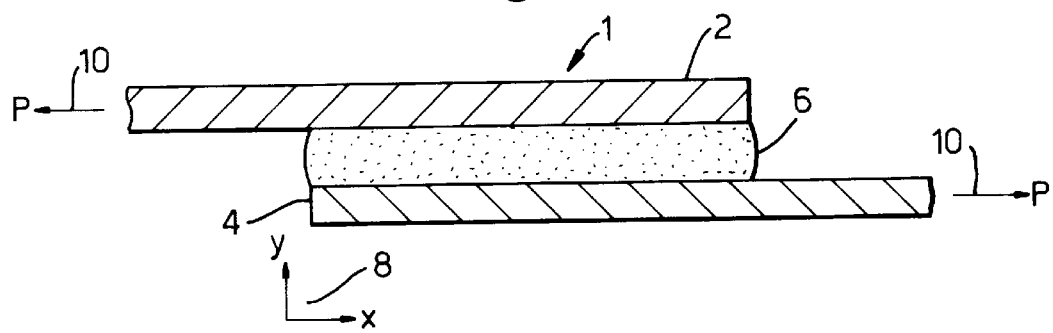
FIG. 1—is a diagrammatic representation of a typical structural bonded lap joint.
Figure 2:
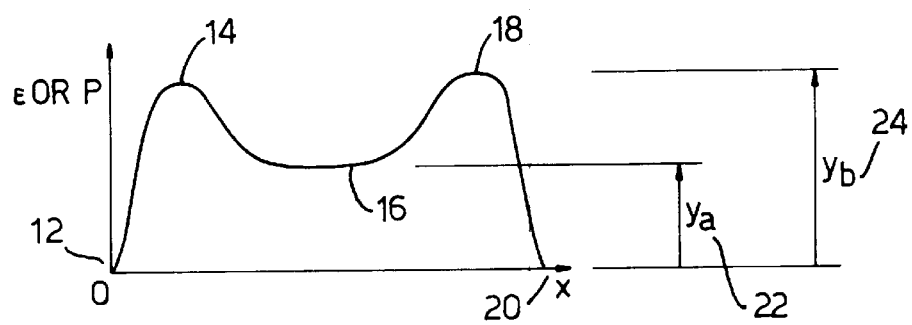
FIG. 2—is a graph showing the typical strain and load distribution for the typical bonded joint shown in FIG. 1.
Figure 3:
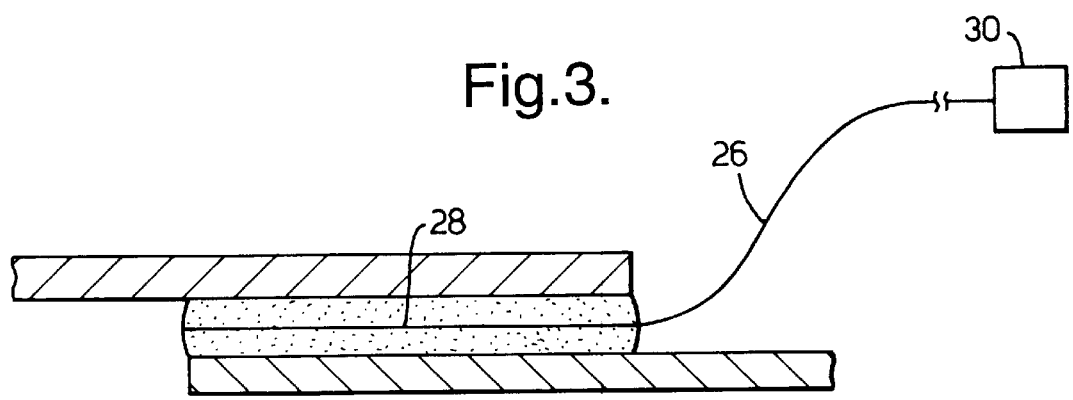
FIG. 3—shows a diagrammatic representation of a joint as in FIG. 1 with the introduction of a sensor means to the joint assembly.

In use, a bonded structural joint which is required to undergo constant, regular or periodic inspection for evaluation of its structural integrity includes a fibre/transducer means 28 embedded in or attached to the adhesive, and connected to a processing/recording/display means 30. Once assembled, the joint is put under load and the characteristic load transfer profile is recorded (e.g., FIG. 2). The parameters of maximum strain or load ($y_b$), 14 and 28, and minimum load ($y_a$) at the centre of the joint 6 is recorded and the ratio of these two parameters calculated. Additionally the shape of the load distribution curve generated between the peaks could be analyzed and a measure of its correlation or standard deviation made to quantify a parameter relating to the "smoothness" or rate of change of load transfer across the bond line. Additionally the positions of these maxima and minima in the x plane also give and indication of changes in the mechanical properties of the joint and bond line due to phenomena such as delamination material/adhesive delamination and adhesive voids or stress concentrations.

Armed with these initial, "at assembly" parameters, the monitoring of the integrity of the joint in service consists of the constant or periodic recording of the load transfer profile characteristics of the joint, and the comparison of newly recorded ratios and curve data with the initial "at assembly" values. The integrity of the bond line is assessed using this innovative technique by comparing the differences in maximum/minimum ratios and curve parameters to those of the "at assembly" values.

The invention will enable the engineer to monitor the performance and integrity of a load carrying bonded joint by comparing the inherent load transfer characteristics of the adhesive material and joined structural members, against a model of the same joint in the original "at assembly" condition. This method therefore is not reliant on known initial data and does not require predictive models of specific material load transfer characteristics, but utilizes the initial properties of such a joint to monitor its degradation with time.

Limited allowable changes in the measured parameters for differing materials can be assessed by structural testing of a range of structural adhesives, with such allowable being developed to meet the requirements of the particular applications to which this novel method of analysis is applied. Examples of industrial applications to which this invention could be applied are numerous and include aerospace, mechanical, civil and automotive engineering, along with any structural adhesive application which requires some form of repeated monitoring of bonded joint integrity.

The fibre/transducer means could take the form of a series of point strain measuring means, or alternatively fibre optic technology could be applied by utilizing integrated or etched gratings. In such a fibre optic grating application, the displacement and or strain characteristics of the bond line material would manifest itself in distortions of the embedded grating with the assembly under load, which, in combination with a method such as optical time domain reflectometry, could therefore be used to measure and record the required load transfer parameters required for joint analysis in accordance with the invention.

Yet another method of obtaining the required bond line data would be the use of an optical, electrical or piezo electric technique whereby measurable changes in material, electrical or optical properties the adhesive itself under applied load, could result in a recordable output or signal which in turn could be processed to produce the required parameters required to apply the invention.

I claim:

1. A method of analyzing the integrity of adhesively bonded structural joints under load, comprising the steps of:

locating a transducer means in proximity of said bonded joint, said transducer means being so disposed in relation to said bonded joint that parameters indicative of load transfer characteristics between a bonded material and an adhesive can be recorded in response to an applied load, wherein said transducer means comprises a fiber optical cable with an integrated optical grating means, said grating means extends parallel with the applied load for indicating strain characteristics alone a bond line of said joint, wherein said load transfer characteristics are measured by optical time domain reflectometry;

recording reference parameters indicative of the load transfer characteristics between the bonded material and the adhesive of said bonded joint under the application of a reference load after assembly of said bonded joint;

subsequently recording service parameters indicative of the load transfer characteristics between the bonded material and the adhesive of said bonded joint under the application of a service load; and comparing said reference parameters with said subsequently obtained service parameters to determine an integrity of the bond.

* * * * *

UNITED STATES PATENT AND TRADEMARK OFFICE
CERTIFICATE OF CORRECTION

PATENT NO. : 5,841,034
DATED : November 24, 1998
INVENTOR(S) : BALL

It is certified that error appears in the above-identified patent and that said Letters Patent is hereby corrected as shown below:

On the title page, insert the following item

--[30] Foreign Application Priority Data

Jul. 7, 1995 [GB] United Kingdom 9513928.3--

Signed and Sealed this

Sixth Day of July, 1999

Attest:

Q. TODD DICKINSON

*Attesting Officer*    *Acting Commissioner of Patents and Trademarks*